United States Patent [19]

Walus

[11] Patent Number: 4,830,001

[45] Date of Patent: May 16, 1989

[54] ASSEMBLY SLEEVE FOR CRANIAL DRILL

[75] Inventor: Richard L. Walus, Norwell, Mass.

[73] Assignee: Codman & Shurtleff, Inc., Randolph, Mass.

[21] Appl. No.: 84,233

[22] Filed: Aug. 10, 1987

[51] Int. Cl.⁴ .............................................. A61B 17/16
[52] U.S. Cl. ................................ 128/310; 128/92 VD; 408/139
[58] Field of Search ............... 128/92 VD, 310, 305.1; 408/14, 15, 703, 139; 403/326

[56] References Cited

U.S. PATENT DOCUMENTS

| | | | |
|---|---|---|---|
| 2,525,669 | 10/1950 | Hainault | 128/310 |
| 3,887,222 | 6/1975 | Hammond | 403/326 X |
| 4,142,543 | 3/1979 | Krause et al. | 403/326 X |
| 4,319,577 | 3/1982 | Bofinger et al. | 128/305.1 |
| 4,362,161 | 12/1982 | Reimels et al. | 128/310 |
| 4,365,696 | 12/1982 | Telford | 403/326 X |
| 4,541,612 | 9/1985 | Yohner | 403/326 X |
| 4,544,425 | 10/1985 | Provolo | 403/326 X |
| 4,699,550 | 10/1987 | Baker | 128/305.1 X |

Primary Examiner—Robert A. Hafer
Assistant Examiner—Kevin G. Rooney
Attorney, Agent, or Firm—Donal B. Tobin

[57] ABSTRACT

A cranial perforator with an internal clutch which is engaged when the drill is placed against a bone surface for drilling and which will automatically release when the drill penetrates the skull. The components of the drill are held together by a plastic sleeve and a retaining ring which is ultrasonically welded to the interior surface of the plastic sleeve.

23 Claims, 7 Drawing Sheets

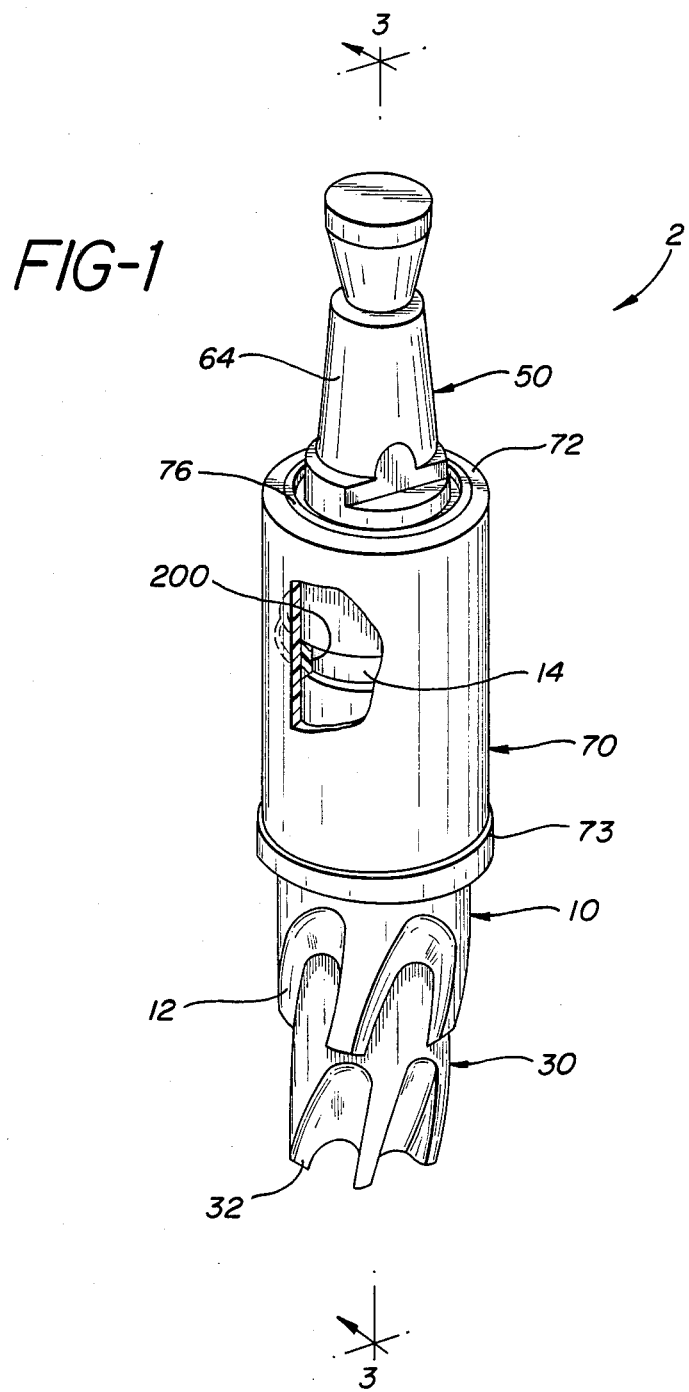

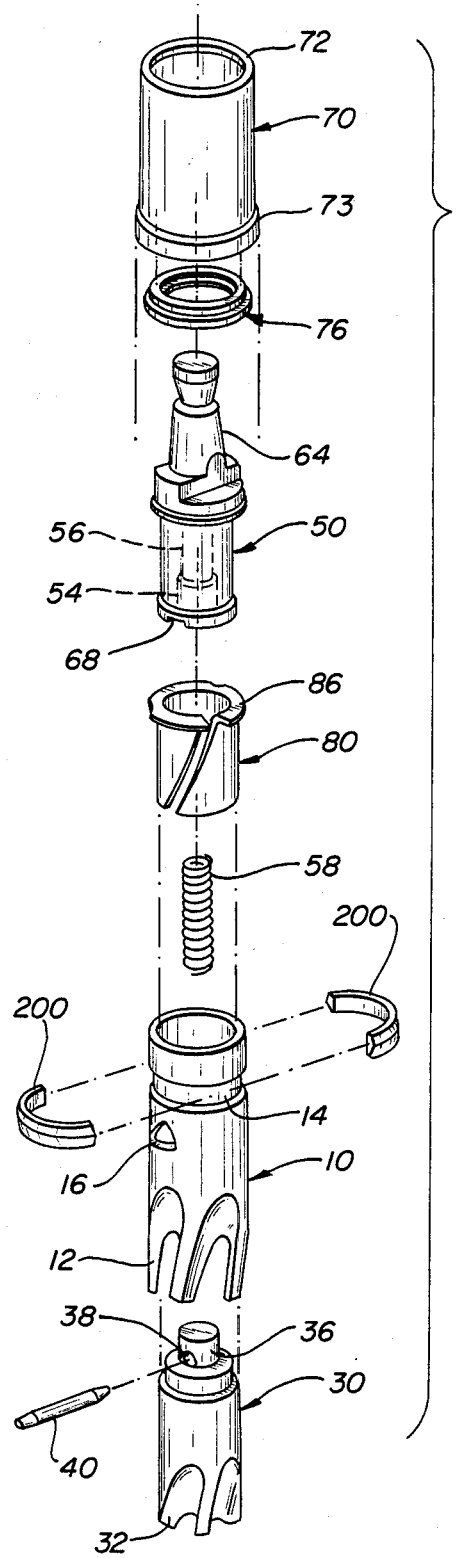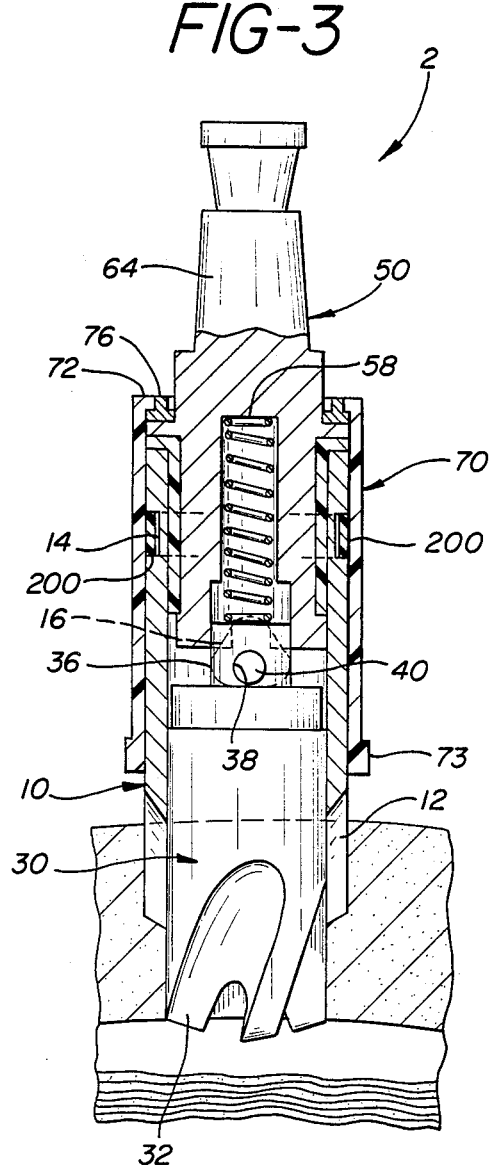

ASSEMBLY SLEEVE FOR CRANIAL DRILL

FIELD OF THE INVENTION

This invention relates to a drill for use by medical practitioners in operations performed on the skull or other bone structure, and more particularly, an improved assembly sleeve for such a drill.

BACKGROUND OF THE INVENTION

In many surgical operations it is necessary to obtain direct access to the cranial cavity and the brain. To perform such operations, it is often necessary to drill holes through the skull bone. Since the bone is very hard, it is necessary to apply significant pressure to drill through it.

A very satisfactory cranial drill with an automatic clutch mechanism for disengaging the drill when it approaches the interior layers of the skull bone or as it breaks through the interior of the skull is described in U.S. Pat. No. 4,456,010, issued June 26, 1984, and assigned to the assignee of the present invention. The disclosure of that patent is fully incorporated by reference in this application.

The invention described in U.S. Pat. No. 4,456,010 incorporates a sleeve about the exterior of the drill for holding the varius parts of the drill together during use. It is described at Column 6, lines 38 through 46 that sleeve 70 of that patent includes a raised portion 74 extending circumferentially on sleeve 70, partially thereabout and is axially aligned with a recess 14 on drill body 10. Raised portion 74 may be deformed radially inwardly to engage recess 14 on drill body 10 to hold sleeve 70 and driver 50 on drill body 10. Although that arrangement works satisfactorily, it has been found that this prior drill can be improved by incorporating a retaining ring in slot 14 shown in the previous patent, assembling the sleeve 70 over drill body 10 and then affixing the retaining ring to the inside surface of the sleeve, preferably by means of ultrasonic welding.

SUMMARY OF THE INVENTION

The present invention is an improvement to the cranial drill as shown in U.S. Pat. No. 4,456,010. That drill includes a primary drill member, a driver with its distal end aligned with the proximal end of the primary drill member, a clutch mechanism connecting the primary drill member and the driver to allow the primary drill member and the driver to rotate together and drill into bone structure and when the clutch is disengaged to permit the primary drill member to remain stationary while the driver rotates. The prior drill also includes an annular drill body into which the primary drill member and the driver slide. The annular drill body includes a recess extending circumferentially about its experior surface. The prior drill also includes an annular sleeve placed about the outer circumference of the drill body and the sleeve has a proximal end which engages the driver. The invention of the present application relates to a retaining ring placed in the annular drill body recess. The ring may be rigidly affixed to the inside wall of the sleeve so that the sleeve is attached to the annular drill body in a way that permits the sleeve to rotate freely with respect to the annular drill body but prevents longitudinal motion between the two. The sleeve holds the drill assembly together. The ring means can be two semicircular rings.

The means for attaching the ring to the inside surface of the sleeve is preferably ultrasonic welding but any method of attachment may be used. If ultrasonic welding is used, the sleeves have an energy directing surface on their outside circumference which is preferably a triangular projection which extends either about the entire circumference of the ring or intermittently about limited portions of each ring. Alternatively the ring can be a C-shaped member which may or may not extend completely about the circumference of the recess in the annular body. If ultrasonic welding is used to hold the C-shape ring to the inside of the sleeve this C-shape ring will also have a similar energy directing taper which can extend about the entire circumference of the C-shape ring or intermittently about that circumference. If the ring extends completely about the circumference of the recess in the annular body, the joint where the ring meets may be specially designed to fascilitate intimate contact by using, for example, a tongue and groove, an angled slit, a jogged slit or some other desirable configuration.

The sleeve and the rings are preferably made of any thermoplastic material particularly ABS plastic but any satisfactory materials that can be permanently fixed together by ultrasonic welding, glueing or any other satisfactory means can be used.

BRIEF DESCRIPTION OF THE DRAWINGS

These and other features and advantages of the present invention will become apparent from the following description of certain embodiments of the invention taken in conjunction with the following drawings in which FIG. 1 is a perspective view of the assembled drill shown partly in section;

FIG. 2 is an exploded perspective of the drill of the present invention;

FIG. 3 is an elevation of the drill of the present invention shown partly in section, taken along line 3—3 of FIG. 1;

DETAILED DESCRIPTION OF THE PREFERRED EMBODIMENT

Figure 4:
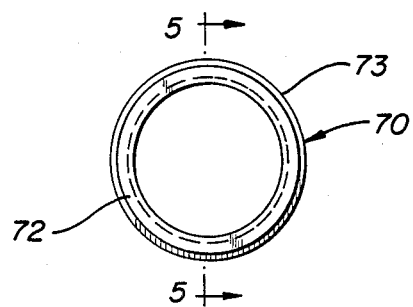
FIG. 4 shows a top plan view of the sleeve element of the present invention.

Referring now to FIG. 1, there is shown a drill assembly 2 of the present invention, which includes a generally annular drill body 10 having counter bore flutes 12 extending from the distal end, a recess 14 extending circumferentially about drill body 10 close to the proximal end in a generally triangular shaped slot 16 extending through diametrically opposed portions of the wall of drill body 10 (see FIG. 2). Generally cylindrical primary drill member 30 fits within the distal end of drill body 10 in a clearance fit so that it may rotate and slide in the axial direction freely. Drill member 30 includes a stem 36 and a transverse bore 38 therethrough. When the primary drill member 30 is assembled within annular drill body 10, pin 40 extends through slot 16 and through transverse bore 38 to hold primary drill member 30 and drill body 10 together.

A generally cylindrical driver 50 fits into the other end of drill body 10. The distal end 52 of driver 50 includes an axial bore 54 and a coaxial pilot bore 56. Transverse slot 68 extends across distal end 52 of driver 50. Pilot bore 56 houses spring 58. Driver 50 includes a chuck stem 64, which is adapted to engage a chuck of a drill.

When driver 50 is inserted in the proximal end of drill body 10 and when slot 68 is aligned with and pushed against pin 40, slot 68 will capture pin 40 to provide a positive drive mechanism for driving driver 50 and primary drill member 30 together. Pin 40 also engages the edges of slot 16 of drill body 10 to drive drill body 10 along with driver 50.

Sleeve 70 fits about the periphery of drill body 10 and includes a flange 72 extending radially inward and circumferentially about the proximal end of sleeve 70 to provide means for holding driver 50 in drill body 10.

The improvement of the present invention over the invention described in U.S. Pat. No. 4,456,010 relates to the way in which sleeve 70 is rotatably connected to drill body 10.

Still referring to FIG. 1, and also to FIG. 2, recess 14 of drill body 10 receives two retaining rings 200 each of which extends approximately half way about the circumference of recess 14. Rings 200 may be ultrasonically welded to the inside surface of sleeve 70 so that each of rings 200 forms a unitary piece with the sleeve 70 to prevent sleeve 70 from moving axially with respect to recess 14 of drill body 10, and thus to hold driver 50 within drill body 10.

Figure 5:
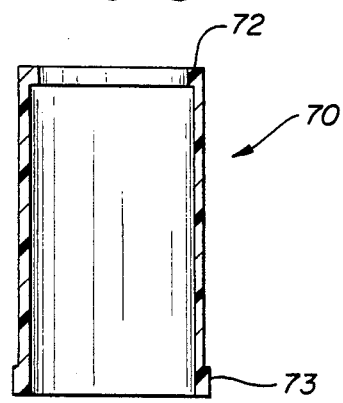
FIG. 5 shows a sectional elevation of the sleeve of FIG. 4, taken along line 5—5 of FIG. 4.

FIGS. 4 and 5 show sleeve 70 which includes inwardly extending flange 72 and outwardly extending flange 73 which extend circumferentially about the distal end of sleeve 70 to act as a stop for the forward motion of drill assembly 2.

Now referring to FIGS. 6, 7 and 8, the details of each ring 200 will now be described. In the preferred embodiment, two semicircular rings 200 are placed in recess 14 to substantially completely fill the circumferential extent of recess 14. The outside circumferential surface of each ring 200 includes an energy directing taper 202 which is essentially triangular in shape with the apex of the triangle located approximately at the center of the longitudinal extent of each ring 200. In the preferred embodiment the energy directing taper extends completely about the circumference of each retaining ring 200 and has a taper of approximately three degrees (3°). This energy directing taper 202 can be a triangular bevel as just described or it can be a convex arch. The material of which each ring 200 is made is any thermoplastic material and preferably ABS plastic, but can be any material which may be permanently attached to the interior surface of sleeve 70. Sleeve 70 is made of any compatible thermosetting plastic but is preferably also made of ABS plastic. The material of which ring 200 and sleeve 70 are made may include any material which is capable of being permanently fixed together.

Figure 9:
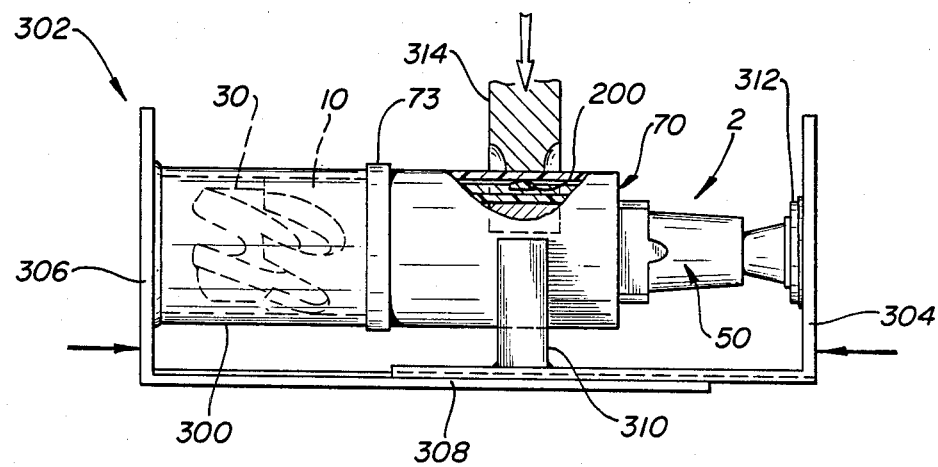
FIG. 9 shows the drill of the present invention in a jig during ultrasonic welding of the sleeve and ring.
Figure 10:
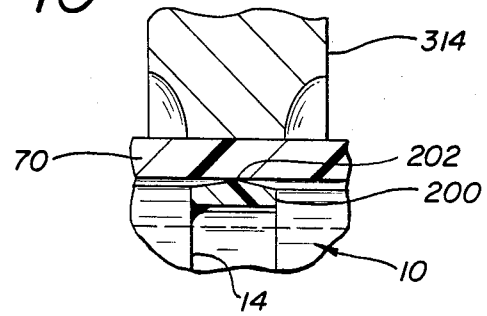
FIG. 10 shows a detailed sectional view of the ultrasonic welder, the sleeve and ring before they are welded together.
Figure 11:
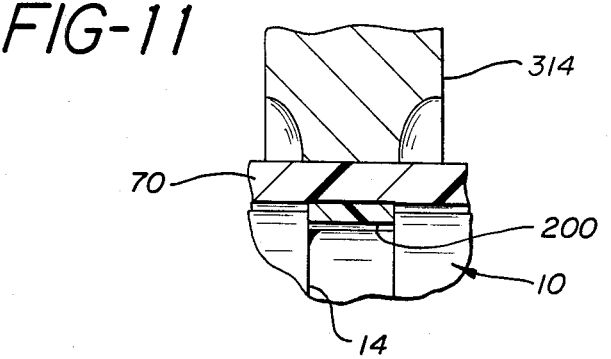
FIG. 11 shows a detailed sectional view of the ultrasonic welder, the sleeve and the ring after they are welded together.

Referring now to FIGS. 9, 10 and 11, the preferred method of fixing rings 200 to the interior surface of sleeve 70 will be described. Ultrasonic bonding is the preferred method of attaching these two parts together, however, any other satisfactory method may be used, for example, gluing. Energy directing taper 202 is used specifically for ultrasonic welding. If gluing were used the energy directing taper 202 could be eliminated.

In preparation for the ultrasonic welding process, two semicircular retaining rings are placed in recess 14 and sleeve 70 is slid into place over the outside of driver 50 and drill body 10. A protective sleeve 300 is slid over primary drill member 30 to protect cutting surfaces 32 and abuts against distal end flange 73 of sleeve 70. The drill is then placed in jig 302 having two L-shaped brackets, 304 and 306, which can slide with respect to one another along a dovetail slot and groove 308 (shown schematically in FIG. 9). A cradle 310 is fixed to one of the L brackets 304 to support sleeve 70 of the drill. A collar 312 supports the proximal end of the drill in jig 302 so that the proximal end of the drill will not move during the ultrasonic bonding process. Sleeve 300 is also affixed to the jig at L-shaped bracket 306 to similarly keep the proximal end of the drill from moving during the ultrasonic bonding process.

Still referring to FIG. 9, an ultrasonic horn 314 includes a generally semicircular recess at its distal end to closely conform to the outside circumference of sleeve 70. The hornm 314 preferably covers about a thirty degree (30°) arc so that only a portion of the ring is welded to the inside of the sleeve. This arc angle is not critical and a greater or lesser arc angle may be used.

During the ultrasonic bonding process, jig 302 is slightly compressed by placing L-shaped bracket 304 and 306 in a vice (not shown) to slightly compress the drill during the ultrasonic bonding process so that spring 58 will create no load on the internal parts of the drill during welding and so that the parts will be properly aligned during welding.

Referring now to FIG. 10, there is shown drill body 10 with retaining ring 200 in position with the energy directing taper 202 contacting the interior surface of sleeve 70 and with the ultrasonic welding horn 314 placed against the outside surface of sleeve 70. It can be seen in FIG. 10 that there is actual contact between energy directing taper 202 and the inside surface of sleeve 70 during the ultrasonic bonding process. In the preferred embodiment two welds are made about one hundred & eighty degrees (180°) apart although more than two welds may be made. For the first weld, the drill assembly is placed in the jig and a weld is made. The drill assembly is then rotated one hundred and eighty degrees (180°) and the second weld is made.

Referring now to FIG. 11, there is shown drill body 10 with ring 200 in place in recess 14 with ring 200 bonded to the interior surface of sleeve 70. It will be noted that there is a radial space between the inside circumferential surface of ring 200 and the outside circumferential surface of recess 14 so that ring 200 may rotate freely within recess 14. There is also a space between the outside circumferential surface of drill body 10 and the inside surface of sleeve 70 so that sleeve 70 may rotate freely about the circumference of drill body 10. Ring 200 is captured within recess 14 so that longitudinal motion of drill body 10 with respect to sleeve 70 is prevented so that sleeve 70 holds the drill together. The axial length of ring 200 is chosen to be comfortably less than the axial length of recess 14 so that ring 200 will not bind as sleeve 70 rotates about drill body 10 when it is welded to ring 200.

Figure 12:
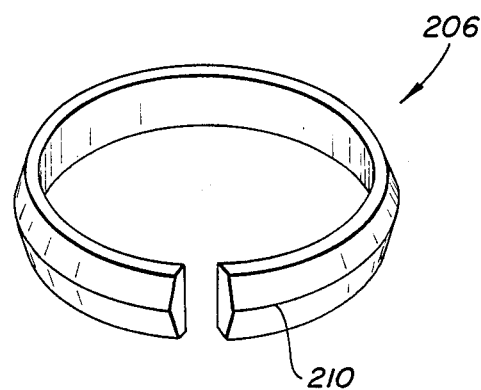
FIG. 12 shows a perspective view of an alternate embodiment of the ring of the present invention.
Figure 13:
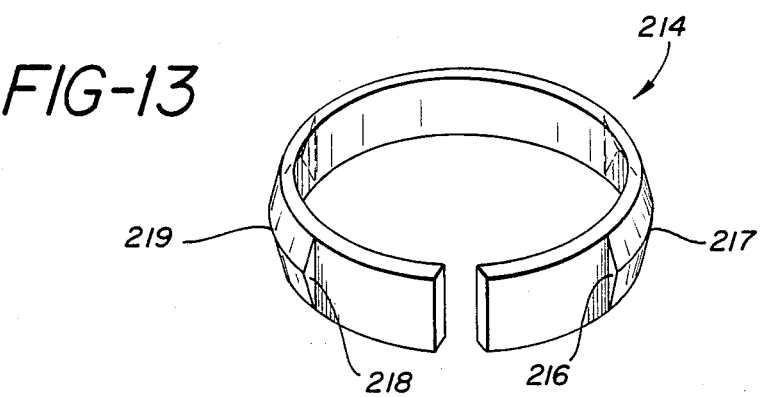
FIG. 13 shows a further alternate embodiment of the ring of the present invention.
Figure 14:
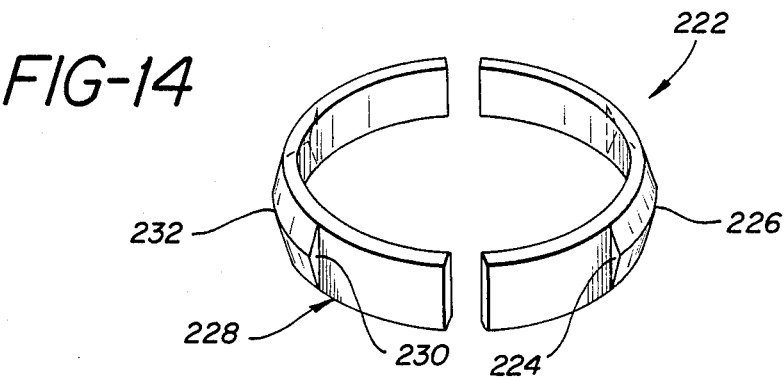
FIG. 14 shows a further alternate embodiment of the ring of the present invention.

Referring now to FIGS. 12 through 14, there are shown alternative embodiments of the retaining ring of the present invention. FIG. 12 shows a single C-shaped retaining ring 206 with an energy directing taper 210 extending completely about the circumference of ring 206 in the same fashion as the energy directing taper 202 of retaining ring 200. Retaining ring 206 is used in the same way as retaining ring 200 except that, when retaining ring 206 is placed in recess 14, it does not cover the entire circumferential extent of recess 14.

Referring now to FIG. 13, there is shown an alternative retaining ring 214 which has the same C-shape as retaining ring 206 except that energy directing taper portions 217 and 219 extend only part way about the outer circumference of ring 214. The triangular shape of the energy directing taper can be seen at end portions 216 and 218 of energy directing tapers 217 and 219, respectively. When ring 214 is used, the weld between the interior surface of sleeve 70 and ring 214 extends only part way about the circumference of the inside surface of sleeve 70, but it is believed that it is sufficient to provide adequate strength at the joint between ring 214 and the interior surface of sleeve 70.

Referring now to FIG. 14, there is shown a further alternative embodiment of the ring of the present invention wherein ring 200 is modified to have an energy directing taper extending only part way along its outer circumferential surface. Two rings, 222 and 228, each have a single energy directing taper 226 and 232, respectively. The triangular shape of the energy directing taper can be seen at the end portion 224 and 230 of energy directing tapers 226 and 232, respectively. Rather than using a single energy directing taper extending part way around the circumference of a ring, multiple energy directing tapers may be spaced along the outer circumferential surface of retaining ring 222 or retaining ring 200.

Referring now to FIGS. 15-18, there shown still further alternative embodiments of the ring of the present invention. Each one of these embodiments provides a special geometry for a single ring which extends completely about the circumstance of recess 14 in annular drill body 10. This feature relates to the slit where the ring comes together. It will be appreciated from FIG. 9 that when the entire drill assembly is inserted in jig 302 ready for ultrasonic welding, the operator cannot see whether the slit in the ring is directly under the ultrasonic welder or not. If the slit is directly under the ultrasonic welder and the ring meets itself at a butt joint running directly transverse to the ring at an angle parallel to the axis of the ring, a slight space can exist so that intimate contact does not occur at the slit.

Figure 15:
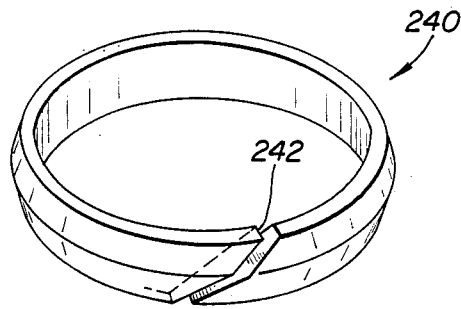
FIGS. 15–18 show alternate embodiment of the ring of the present invention; and, FIGS. 19-22 show an alternate embodiment of the present invention.

Referring now to FIG. 15, there is shown an alternative ring 240 with an angled slit 242 cut in the direction which is not parallel to the axis of ring 240. Thus, if the inner diameter of ring 240 in the relaxed condition is slightly less than the outer diameter of recess 14 in annular drill body 40, no gap will exist at angle slit 242 and the ring can intimately contact itself at slit 242 to provide a more secure ultrasonic bond even if slit 242 is directly under the ultrasonic welding horn 314.

Figure 16:
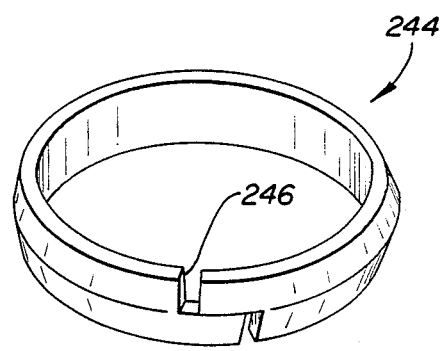

FIG. 16 shows an alternative ring 244 with a jogged slit 246 so that jogged slit 246 similarly permits ring 244 to intimately contact itself even if it is a little smaller than recess 14.

Figure 17:
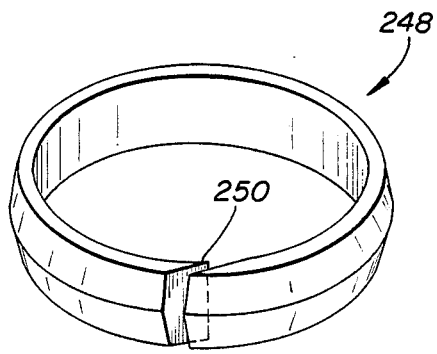

FIG. 17 shows a further alternative ring 248 with a axially angled slit 250 to similarly permit ring 248 to intimately contact itself even if it is smaller than recess 14.

Figure 18:
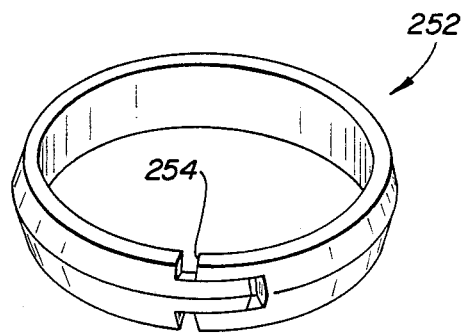

FIG. 18 shows a further alternative ring 252 with a tongue and groove type slit 254.

Figure 6:
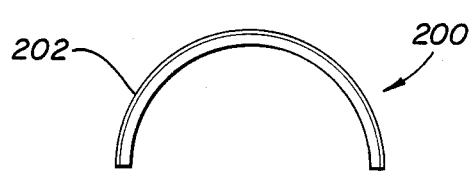
FIG. 6 shows a top plan view of one embodiment of the ring of the present invention.
Figure 7:
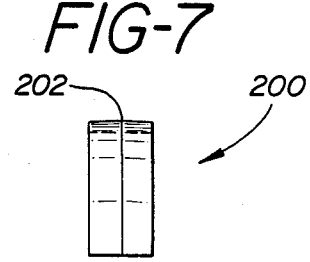
FIG. 7 shows a side elevation of the ring of the present invention.
Figure 8:
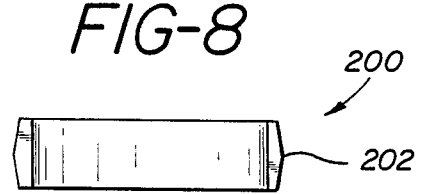
FIG. 8 shows a front view of the ring of the present invention.

These same types of slits or combination of these slits may be used on semi-circular rings 200 shown in FIGS. 6, 7 and 8 to permit the same intimate contact between the two rings even if they are a little smaller than recess 14.

Figure 19:
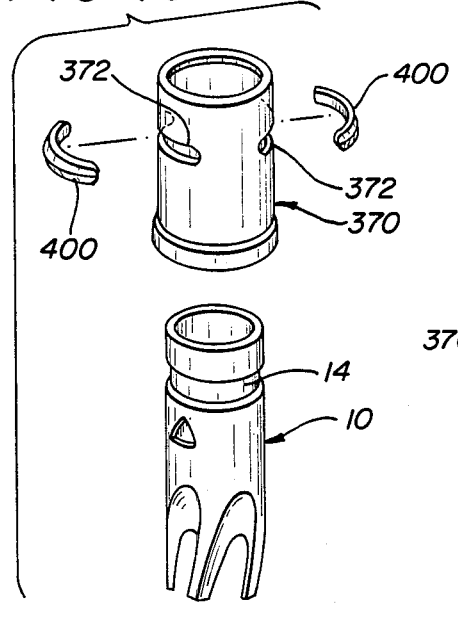

Referring now to FIGS. 19-22, there is shown a further embodiment of the retaining ring and sleeve drill assembly of the present invention. FIG. 19 is an exploded perspective view of a modified sleeve 370 with two slots 372 on diametrically opposed portions of sleeve 370 extending completely through the wall of sleeve 370. Alternatively, more than two slots 372 may be used. Annular drill body 10 with recess 14 is the same as annular drill body 10 for the embodiment of FIGS. 1-3. One modified ring 400 fits into each of slots 372 to act as a key inserted into recess 14. Modified ring 400 is an arcuate ring extending on an arc of about thirty degrees (30°) and is slightly smaller in its outer dimension than the inside dimension of slot 370 so that modified ring 400 may fit easily but snugly into slot 372. The radial thickness of modified ring 400 is slightly greater than the combined depth of recess 14 plus the wall thickness of sleeve 370. Modified ring 400 may be secured into slot 372 by ultrasonic welding or adhesive bonding as with the previous embodiment.

Figure 20:
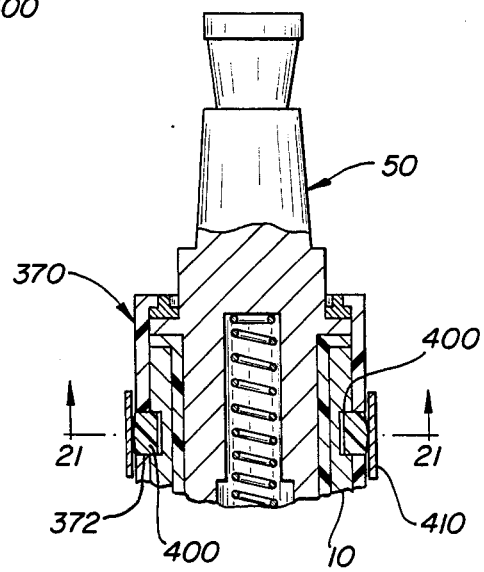
Figure 21:
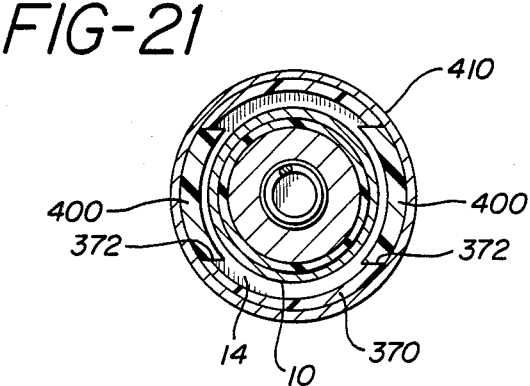
Figure 22:
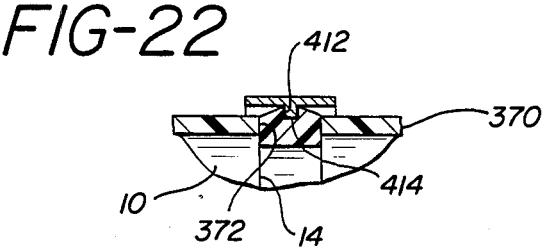

Alternatively, as shown particularly in FIG. 20 and 22 a retaining collar 410 extending completely about the circumference of sleeve 370 over slots 372 and modified ring 400 may be used to hold ring 400 in place. A special energy directing slot 412 extending about the arcuate circumference of each ring 400 will except a corresponding projection 414 extending radially inward from the inside surface of retaining collar 410. Preferably retaining collar 410 and rings 400 are both made of a thermoplastic material particularly ABS plastic so that they may be ultrasonically bonded together in a fashion similar to that of the embodiment of FIGS. 1-3 by a process similar to that described in connection with FIGS. 9-11. The energy directing bevel shown in FIGS. 6-8 could be used on the outer circumferential surface of modified ring 400 instead of slot 412 and projection 414 as just described. Alternatively, retaining collar 410 could be made of metal and a mechanical connection could be made between the inside surface of metal retaining collar 410 and plastic modified ring 400.

Either collar 410 or ring 400 must be made of a thermoplastic material so that if the assembled finished drill were attempted to be sterilized by heat or steam the thermoplastic material would melt and destroy the drill so that it could not be used again. As described earlier in the application, the particular assembly procedure for this drill is to preferably prohibit the drill from being reused after sterilization. If one attempts to sterilize this drill by heat or steam, the thermoplastic material holding the drill together will melt and destroy the drill thus, the expense of disassembly, cleaning and sterilization and the possible risk of incorrect reassembly are avoided.

While the present invention has been described in connection with certain preferred embodiments, those skilled in the art will appreciate that certain modifications may be made without departing from the scope of the present invention. It is, therefore, not intended that the present invention be limited except as set forth in the following claims.

I claim:

1. In an apparatus for drilling bone structure comprising:
   a generally cylindrical primary drill member having a distal end and having a proximal end;
   a generally cylindrical driver having a distal end disposed in confronting relationship to said primary drill member and having a proximal end;
   clutch means cooperatively disposed between said primary drill member and said driver whereby when said clutch means is engaged, said drill member and said driver rotate as a unit and drill into the bone structure, and when said clutch is disengaged, said primary drill member remains stationary as said driver rotates;
   an annular drill body slideably and rotatably receiving said primary drill member and said driver, said annular drill member including a recess extending around the exterior surface of said annular drill body;
   an annular sleeve disposed about said drill body having a proximal end operatively engaging said driver;
   the improvement comprising:
   discrete, arcuate retaining ring means having a medial portion and two edge portions disposed in said annular drill body recess and having means to be rigidly affixed to said sleeve for holding said driver and said annular drill body together against forces exerted in the axial direction;
   said retaining ring means when so bonded being freely rotatable in said annular drill body recess so as not to inhibit the rotational motion of said sleeve with respect to said annular drill body; and
   wherein the outer circumferential surface of said retaining ring means before being so bonded confronts the interior surface of said sleeve and includes an energy directing means including an outwardly extending generally triangular taper on its outer periphery with the medial portion of said retaining ring means being thicker than the two edge portions.

2. The apparatus of claim 1 wherein said retaining ring means includes two substantially semicircular retaining rings.

3. The apparatus of claim 1 wherein said retaining ring means is affixed to said sleeve by means of ultrasonic welding.

4. The apparatus of claim 1 where said energy directing means extends around the entire periphery of said retaining ring means.

5. The apparatus of claim 1 wherein said energy directing means extnds only part way around the circumference of said retaining ring means.

6. The apparatus of claim 1 wherein said retaining ring means is a single, unitary C-shaped member.

7. The apparatus of claim 6 wherein said C-shaped retaining ring means includes energy directing means on its outer periphery.

8. The apparatus of claim 7 wherein said energy directing means extends about the entire periphery of said C-shaped retaining ring means.

9. The apparatus of claim 6 wherein said energy directing means extends only part way about the outer periphery of said C-shaped retaining ring means.

10. The apparatus of claim 1 wherein said annular sleeve includes at least two arcuate slots extend about at least a portion of the circumference of said sleeve and extending completely through the wall of said sleeve;
    wherein said retaining ring means include a discrete, arcuate member disposed in each of said slots in said annular sleeve and extending into said annular drill body recess.

11. The apparatus of claim 10 wherein said member and said sleeve are bonded together.

12. The apparatus of claim 11 wherein said bonding includes ultrasonic bonding.

13. The apparatus of claim 10 further including a retaining collar disposed about the circumference of said sleeve and aligned over said slots in contact with said members to hold said members in said slots.

14. The apparatus of claim 13 wherein said retaining collar and said members are ultrasonically bonded together.

15. The apparatus of claim 13 wherein said retaining collar and said sleeve are ultrasonically bonded together.

16. The apparatus of claim 13 wherein said retaining collar, said members and said sleeve are ultrasonically bonded together.

17. The apparatus of claim 13 wherein said retaining collar and said members are mechanically connected together.

18. The apparatus of claim 13 wherein the outer circumferencial surface of said member further includes an energy directing means facing the confronting surface of said retaining collar.

19. The apparatus of claim 1 wherein said retaining ring means is a unitary annular ring having a slit there through to allow said ring to be assembled about said annular drill body in said recess;
    said slit being arranged to allow the opposite sides of the slit to have intimate contact with each other even though the ring, when assembled in said recess may have a inner diameter slightly less than the outer diameter of said recess.

20. The apparatus of claim 19 wherein said slit includes an angled slit generally perpendicular to the inner circumference to the annular ring and at an angle to the axis of the ring.

21. The apparatus of claim 19 wherein said slit is an angled slit extending in the direction generally parallel to the axis of said annular ring but at an angle to the tangent to the inner circumferencial surface of said ring at the place where said slit penetrates the inner circumferencial surface of said ring.

22. The apparatus of claim 19 wherein said slit is a jogged slit.

23. The apparatus of claim 19 wherein said slit includes a tongue and groove joint.

* * * * *